United States Patent [19]

Wheelock

[11] 4,219,447

[45] Aug. 26, 1980

[54] CATALYST AND A PROCESS FOR ITS PREPARATION

[75] Inventor: Kenneth S. Wheelock, Baton Rouge, La.

[73] Assignee: Exxon Research & Engineering Co., Florham Park, N.J.

[21] Appl. No.: 970,936

[22] Filed: Dec. 19, 1978

[51] Int. Cl.$^2$ .................... B01J 21/04; B01J 23/40; B01J 23/42

[52] U.S. Cl. .................... 252/466 PT; 252/472

[58] Field of Search ................ 252/463, 466 PT, 460, 252/472

[56] References Cited

U.S. PATENT DOCUMENTS

| | | | |
|---|---|---|---|
| 3,184,415 | 5/1965 | Huntley et al. | 252/463 X |
| 3,943,050 | 3/1976 | Bertolacini et al. | 208/138 X |
| 3,945,946 | 3/1976 | Hindin et al. | 252/466 PT |
| 3,953,368 | 4/1976 | Sinfelt | 252/466 PT |
| 3,997,431 | 12/1976 | Beuther et al. | 208/216 R |

Primary Examiner—W. J. Shine
Attorney, Agent, or Firm—Llewellyn A. Proctor

[57] ABSTRACT

A novel catalyst precursor which comprises a Group IV-B transition metal oxide deposited on the surface of an inorganic metal oxide support, preferably alumina; especially where the Group IV-B transition metal oxide is deposited on the support surface as discrete areas separated by areas of support surface which contain little, if any, of said Group IV-B transition metal oxide; and a catalyst composition comprised of a cluster of a Group IV-B transition metal oxide and a Group VIII metal preferably a Group VIII noble metal, deposited on an inorganic metal oxide support, particularly an alumina support, especially where the clusters are deposited on the surface of the support, as discrete clusters separated by areas of support surface which contain little, if any, of said Group VI-B transition metal oxide, or clusters of said Group IV-B and Group VIII metals.

14 Claims, 1 Drawing Figure

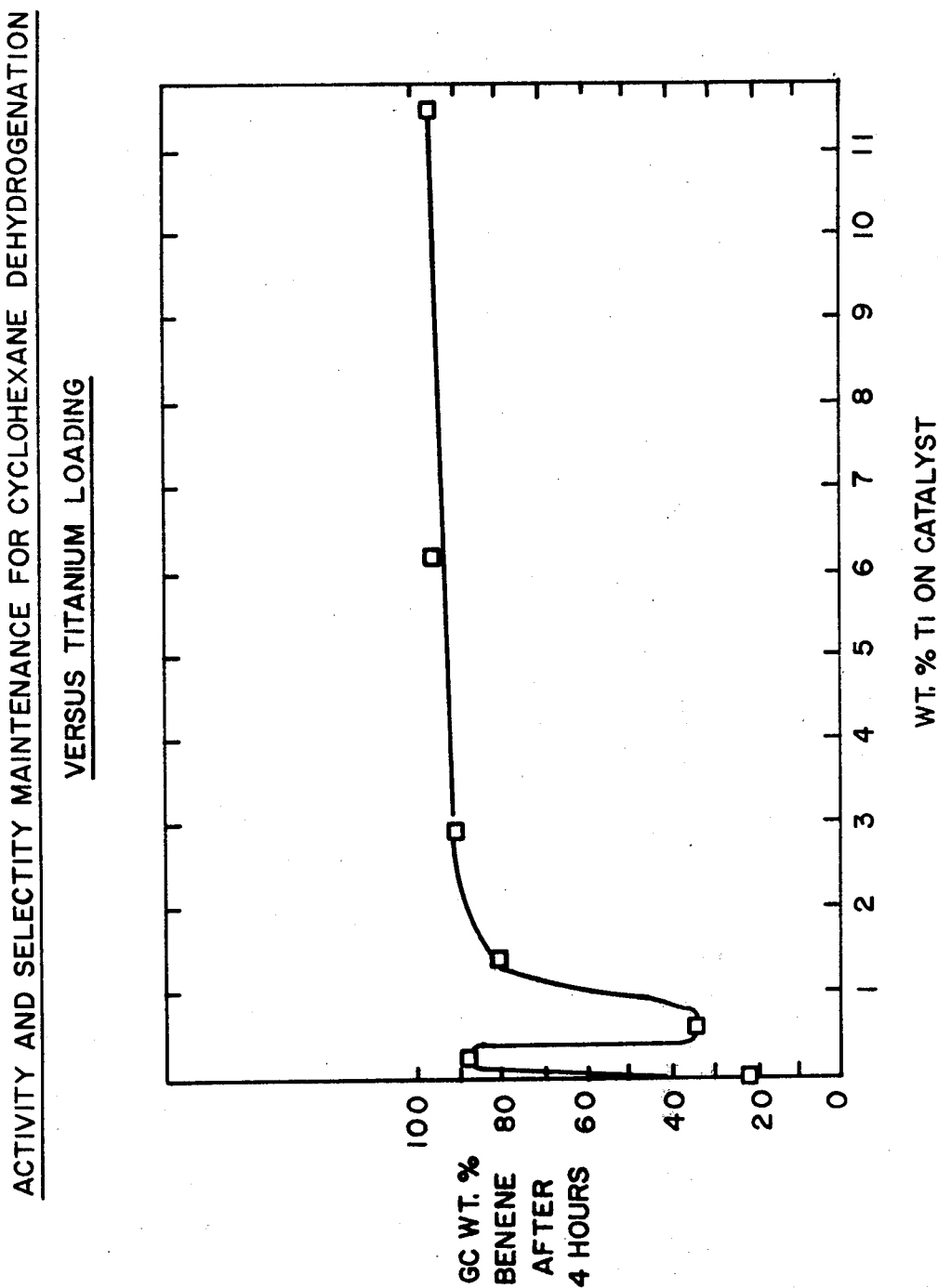

CATALYST AND A PROCESS FOR ITS PREPARATION

Various catalysts are commercially employed in the petroleum and petrochemical industry in which an activating metal, or metal oxide, is composited with a porous inorganic metal oxide support, notably alumina. The presence of the metal, or metal oxide, is often used to impart a hydrogenation-dehydrogenation (hydrogen transfer) function to the catalyst, and other components are often added with the metal component, or components, to provide other functions. Polyfunctional catalysts are thus often used to provide a variety of conversion reactions such as isomerization, hydroisomerization, cyclization, polymerization, and the like.

In many catalytic processes more than one of these reactions are thus produced simultaneously by compositing various components with a support. In reforming (hydroforming), for example, a feed comprised of an admixture of paraffins and naphthenes is contacted in the presence of hydrogen with a catalyst composite comprised of a Group VIII noble metal, with or without the additional presence of other promoter metals, in halogen component, and an inorganic oxide support. The noble metal, or metals, component provides a hydrogenation-dehydrogenation function, isomerization function, hydrocracking function and/or hydrogenolysis function, and the halogen component, which is acidic, provides isomerization, cracking, and/or hydrocracking functions.

During such reactions a carbonaceous, or coke deposit is formed and gradually laid down on the catalyst, this interfering with the activity and stability of the catalyst. The coke accumulation on the catalyst begins at start-up of the process, and accordingly a gradual increase in the process temperature is required to compensate for the gradual loss of catalyst activity caused by the coke deposition. Eventually however, process economics dictate shutdown of the process so that the catalyst can be regenerated by burning or otherwise removing the coke deposits from the catalyst, or the charging of a fresh catalyst to the unit. In consequence thereof, the temperature increase per unit time required to maintain a constant catalyst activity during an operating run, i.e., the Temperature Increase Requirement (TIR), thus represents an important consideration in the development and manufacture of commercial catalysts.

Accordingly, it is the basic objective of the present invention to provide new and improved catalyst compositions, a process for the preparation of new and improved catalysts of good activity and stability, and process for the use of these catalysts to conduct hydrocarbon conversion reactions.

In particular, it is an object to provide novel catalyst precursor compositions, and catalyst compositions useful for conducting a variety of hydrocarbon conversion reactions, especially hydrogen transfer reactions, with relatively low TIR requirements.

These objects and others are achieved in accordance with the present invention which embodies (i) a catalyst precursor composition, comprised of a Group IV-B transition metal oxide, (or admixture thereof) deposited on the surface of an inorganic metal oxide support, preferably alumina; especially a Group IV-B transition metal oxide (or admixture thereof) deposited on the support surface as discrete areas, patches or islands separated by areas of support surface which contain little, if any, of said Group IV-B transition metal oxide;

(ii) a catalyst composition comprised of a cluster of a Group IV-B transition metal oxide (or admixture thereof) and a Group VIII metal (or admixture thereof), preferably a Group VIII noble metal (or admixture thereof) especially a Group VIII noble metal of even atomic number, particularly paladium and platinum, deposited on an inorganic oxide support, particularly alumina, especially where the clusters are deposited on the surface of the support as discrete clusters separated by areas of support surface which contain little, if any, of said Group IV-B transition metal oxide, or clusters of said Group IV-B and Group VIII noble metals;

(iii) a process for the preparation of the catalyst precursor compositions characterized in (i), supra, which comprises forming a nonaqueous solution of a compound, or compounds, of a Group IV-B metal, preferably a hydrocarbon solution, and more preferably a normally liquid paraffin solution of a compound of said Group IV-B transition metal, contacting said solution with an inorganic metal oxide support, preferably an alumina support, to impregnate said solution into said support, drying and then calcining said support in a moist atmosphere to form and deposit said Group IV-B transition metal oxide onto said support surface, preferably as discrete areas of support surface constituting patches, or islands of Group IV-B transition metal oxide surrounded by areas which contain little, if any, of said Group IV-B transition metal oxide;

(iv) a process for the preparation of a catalyst composition comprised of a cluster of a Group IV-B transition metal oxide (or admixture thereof) and a Group VIII metal (or admixture thereof), preferably a Group VIII noble metal (or admixture thereof), especially a Group VIII noble metal of even atomic number, particularly palladium and platinum, composited with an inorganic oxide support, preferably alumina, especially where the clusters are deposited on the surface of the support as discrete clusters separated by areas of support surface which contain little, if any, of said Group IV-B transition metal oxide, or clusters of said Group IV-B transition metal oxide and Group VIII metal, which comprises impregnating said precursor catalyst composition of (i), supra, by contact therewith of a solution of a Group VIII noble metal compound (or admixture thereof), and thereafter drying and calcining said composite; and (v) a process for the conversion of a hydrocarbon feed by contact threof at hydrocarbon conversion conditions with a catalyst composite as characterized in (ii), supra.

The catalyst precursor compositions, as characterized in (i), supra, are prepared by contacting and impregnating an inorganic metal oxide support, preferably alumina, suitably at temperatures ranging from about 32° F. to about 212° F., preferably from about 60° F. to about 90° F., with a nonaqueous, nonhalogen containing solution of a compound of a Group IV-B transition metal, e.g., a compound of titanium, zirconium, or hafnium, or combinations thereof, to deposit a sufficient amount thereof to provide from about 1.5 percent to about 2.5 percent, preferably from about 4.5 percent to about 20 percent, of the metal onto the support calculated as metal oxide, based on the total weight of the composition (dry basis). The support is impregnated with the solution, preferably by incipient wetness techniques, and then contacted with a moist atmosphere, or atmosphere containing water in concentration ranging from about 50 to about 100% relative humidity, preferably from about 60 to about 100 relative humidity, suitably at temperatures ranging from about 32° F. to about 212° F., preferably from about 60° F. to about 90° F., sufficient to form the metal oxide. The support is then calcined at temperatures ranging from about 800° F. to about 1800° F., but below the sintering temperature of the support, preferably from about 1000° F. to about 1200° F., suitably for periods ranging from about 0.5 to about 24 hours, preferably from about 2 to about 4 hours.

The Group IV-B transition metal compound can be virtually any which is soluble in an nonaqueous solvent, preferably a paraffinic hydrocarbon solvent. The anionic constituent of the transition metal compound can be polar or nonpolar. Preferably, the anionic constituent in one such as found in weak organic acids, e.g., acetates, propionates, butyrates, valerates and the like; or other fatty acid radicals, e.g., stearates, laurates, oleates and the like; or salts of alcohols, e.g., butanols, hexanols, octanols, glycols and the like. More preferably the anionic constituent of the transition metal compound is an alkoxide, e.g., ethoxide, benzoate and the like. Exemplarly of preferred Group IV-B transition metal compounds are titanium tetraisopropylate, zirconium tetraisopropylate, halfnium tetra-n-propylate, titanium tetraisobutylate and the like.

The nonaqueous solvent within which the Group IV-B transition metal compound is dissolved, like the anionic constituent of the Group IV-B transition metal compound can be polar or nonpolar. Exemplary of solvents useful for this purpose are ethers, e.g., diethylether, dioxane, tetrahydrofuran, and the like; ketones, e.g., acetone, methyl ethyl ketone, methyl isobutyl ketone and the like; alcohols, e.g., methanol, propanol, and the like; amines, e.g., diethyl amine, tetra propyl amine, and the like; paraffins, cycloparaffins, and isoparaffins, e.g., $C_5-C_{20}$ saturated paraffins such as pentane, isooctane, cyclohexane, decane, dodecane, cyclododecane and the like; and $C_6-C_{20}$ aromatics, e.g., benzene, xylene, durene, ethyl benzene and the like.

Supports useful in the practice of this invention may be naturally occurring or synthetically prepared, preferably the latter, and they are comprised of porous inorganic oxides such as alumina, silica, magnesia, thoria, boria, zirconia, aluminosilicates, such as zeolites, and the like. Mixtures of these can be used such as silica and alumina, magnesia and alumina, magnesia and zirconia, alumina and boria, alumina and alumino silicate, silica and magnesia and the like. Alumina is preferred, a suitable alumina being one formed of suitable size and shaped as pellets, spheres, pills, beads, extrudates or the like. A sol type alumina is quite useful for purposes of this invention and can be prepared by gelling and drying an aqueous sol, or the alumina can be obtained by neutralizing an aqueous alkali metal aluminate or aluminum salt solution with a base, or with ehtylene oxide, followed by washing, drying and calcining the resulting aluminum hydroxide precipitate.

The catalyst compositions, as characterized in (ii), supra, are prepared by contacting and impregnating the dried, calcined catalyst precursor composition of (i), supra, with a solution within which is dissolved a compound, or compounds, which contains a Group VIII metal, notably a Group VIII noble metal, or platinum group metal component such as ruthenium, rhodium, palladium, osmium, platinum, or the like. Of these latter class of metals, platinum and palladium are the preferred components, and platinum-titanium, platinum-zirconium, palladium-titanium, and palladium-zirconium are the preferred species of catalysts.

An additional metallic component, or components, can be added as a promoter metal if desired; suitably a component selected from the Group IV metals (Ge, Sn, Pb), Group VI metals (Cr, Mo, W), Group VII metals, the Group VIII metals. For example, germanium, tin, lead, osmium, ruthenium, or rhodium can be used. Although one or more of these components can be added by any of the conventional methods, it is preferable to add them by impregnation following or simultaneously with the impregnation of the Group VIII metal. The promoter metal, or metals are added in concentration ranging about 0.01 to 3 percent, preferably from about 0.03 to about 1 percent, based on the weight of the catalyst.

The Group VIII metal hydrogenation-dehydrogenation or promoter metal components can be composited or intimately associated with the porous inorganic oxide support or carrier by various techniques known in the art such as ion-exchange, coprecipitation with the alumina in the sol or gel form, and the like. For example, the catalyst composite can be formed initially by adding together suitable reagents such as a salt of platinum and ammonium hydroxide or ammonium carbonate, and a salt of aluminum such as aluminum chloride or aluminum sulfate to form aluminum hydroxide. The aluminum hydroxide containing the salts of platinum can then be heated, dried, formed into pellets or extruded, and then calcined.

It is much more preferred, however, to deposit the Group VIII metal, or metals, and metals used as promoters, on a previously pilled, pelleted, beaded, extruded, or sieved particulate support material by the impregnation method after the Group IV-B transition metal oxide has been formed on the support surface. In the impregnation method, a porous refractory inorganic oxide in dry or solvated state is contacted typically via an "incipient wetness" technique which requires a minimum of solution so that the total solution is absorbed, initially or after some evaporation, the objective being to effect as much as possible near total uptake of the metallic components by absorption of the liquid.

The Group VIII metal component is supported on the carrier within the range of from about 0.01 to 3 percent, preferably from about 0.05 to 1 percent, based on the weight of the catalyst. In compositing the Group VIII metal with the carrier, essentially any soluble compound can be used, but a soluble compound which can be easily subjected to thermal decomposition and reduction is preferred. For example, where the Group VIII metal is platinum, platinum nitrate, platinum polyamine, platinum acetylacetonate, and the like, are preferably used.

The impregnation solution of the Group VIII metal compound, notably the Group VIII noble metal compound and metals used as promoters, if any, are prepared by dissolving the compound in water or other inorganic or organic solvent. The concentration of the metallic component in the solution generally ranges from about 0.01 to 5 percent, preferably from about 0.05 to 1 percent, based on the weight of solution. The pH of the impregnation solution containing the noble metal compound should be controlled to less than about 4, preferably less than 3, by the addition of a suitable inorganic or organic acid. By controlling the pH within these ranges, the components can be more effectively dispersed into the inner part of the catalyst.

In a preferred embodiment of the present invention a carrier can be impregnated with an aqueous solution of the a compound of Group VIII metal, notably a Group VIII noble metal followed by evaporation or filtration and then drying or calcination, or both. To enhance catalyst performance, it may also be required to add a halogen component. Chlorine is a preferred halogen component. The halogenn is added to the catalyst whithin the range of 0.1 to 3 percent, preferably within the range of about 0.3 to 2 percent, based on the weight of the catalyst. When using chlorine as a halogen component, it is contained on the catalyst within the range of about 0.2 to 2 percent, preferably within the range of about 0.5 to 1.5 percent; based on the weight of the catalyst. The halogen may be introduced in any one of several manners, e.g., by contacting a carrier material in a vapor phase or liquid phase with a halogen compound such as hydrogen fluoride, hydrogen chloride, ammonium chloride, or the like.

The catalyst is dried by heating at a temperature above about 80° F., preferably between about 150° F. and 300° F., in the presence of nitrogen or oxygen, or both, in an air stream or under vacuum. The catalyst is calcined at a temperature between about 500° F. to 1200° F., preferably about 500° F. to 1000° F., either in the presence of oxygen in an air stream or in the presence of an inert gas such as nitrogen.

The feed or charge stock for use in conducting a reforming reaction can be virgin naphtha, cracked naphtha, a Fischer-Tropsch naphtha, or the like. Typical feeds are those hydrocarbons containing from about 5 to 12 carbon atoms, or more preferably from about 6 to about 9 carbon atoms. Naphthas, or petroleum fractions boiling within the range of from about 80° F. to about 450° F., and preferably from about 125° F. to about 375° F., contain hydrocarbons of carbon numbers within these ranges. Typical fraction thus usually contain from about 20 to about 80 vol.% paraffins, both normal and branched, which fall in the range of about $C_5$ to $C_{12}$, from about 10 to 80 vol.% of naphthenes falling within the range of from about $C_6$ to $C_{12}$, and from 5 through 20 vol.% of the desirable aromatics falling within the range of from about $C_6$ to $C_{12}$.

In conducting reforming runs, the runs are initiated by adjusting the hydrogen and feed rates, and the temperature and pressure to operating conditions. The run is contianued at optimum reforming conditions by adjustment of the major process variables, within the ranges described below:

| Major Operating Variables | Typical Process Conditions | Preferred Process Conditions |
|---|---|---|
| Pressure, Psig | 50–750 | 100–300 |
| Reactor Temp., °F. | 750–1100 | 850–1000 |
| Gas Rate, SCF/B (Incl. Recycle Gas) | 1500–10,000 | 2000–7000 |
| Feed Rate, W/W/Hr | 0.5–10 | 1–3 |

The invention will be more fully understood by reference to the following nonlimiting examples which present comparative data illustrating its more salient features. All parts are given in terms of weight except as otherwise specified.

BRIEF DESCRIPTION OF THE DRAWING

Reference is made to the attached FIGURE. The FIGURE graphically represents runs made with a cyclohexane feed passed over catalysts of varying titanium content to produce benzene. The graph illustrates the initiation of a stabilizing interaction between Pt and some form of Ti which increases with increasing Ti content reaching 90% of the effect at Ti loadings as low as 1.5 wt% Ti.

In conducting the runs catalysts were first prepared, and certain selected feeds, i.e., cyclohexane, methyl cyclopentane, and normal heptane were reactd thereover to determine the specific types of catalytic activity. The types of reactions known to predominate in reforming, are the (1) dehydrogenation of cyclohexane and substituted cyclohexanes to form benzene and alkylbenzenes, (2) isomerization of methylcyclopentane and its derivatives to form cyclohexane or its derivatives followed by dehydrogenation to form aromatics, and (3) cyclization of $C_6+$($C_6$ and greater) straight chain paraffins to form cyclohexane derivatives followed by dehydrogenation to form aromatics. These reactions are selected to serve as models and enable a point by point comparison of various significant factors of interest for the different catalysts. The desired activity of a catalyst is thus measured by the dehydrogenation of cyclohexane to produce benzene, the isomerization of methylcyclopentane to produce benzene, the dehydrocyclization of normal heptane to produce toluene, and hydrogenation of benzene to produce cyclohexane.

Since it is known in the art that low pressures accelerate catalyst deactivation, choice of low pressures for comparative evaluations are utilized to enable a temporal compression which facilitates comparison especially when the comparison is made against a known reference having the desired catalytic activities as evidenced by choosing as that reference a commercially successful catalyst.

Catalyst testing was carried out in a small atmospheric pressure unit to which small amounts of an appropriate pure hydrocarbon and carrier gas, either hydrogen or helium, was fed. The hydrocarbon vapors were entrained in the carrier gas and fed at calibrated, carefully controlled rates to the reactor which contained one cc of catalyst (20–40 mesh) as a catalyst charge.

The gas hydrocarbon mixture after contact with the catalyst exits the reactor through heated lines past a septum sampling port to a wet tester meter used for monitoring total gas flow. Product samples were taken periodically by inserting a heated syringe through the septum port and withdrawing a gaseous sample of the product. Product analysis of the hydrocarbon portion of the product was conducted by gas chromatography.

The following conditions were employed in obtaining the data, to wit:

| Reaction | Atmosphere | W/Hr/W (0.7 g Catalyst) | Temp. |
|---|---|---|---|
| Cyclohexane dehydrogenation | $H_2$ | 1.3 | 495° C. |
| Methycyclopentane conversion to benzene | $H_2$ | 3.0 | 495° C. |
| Normal heptane dehydrocyclization to toluene | $H_2$ | 1.3 | 495° C. |
| Benzene hydrogenation to | | | |

| Reaction | Atmosphere | W/Hr/W (0.7 g Catalyst) | Temp. |
|---|---|---|---|
| cyclohexane | $H_2$ | 2.2 | 150° C. |

EXAMPLE 1

A catalyst, Catalyst A, was prepared by immersing a high surface area (185 m²/g ± 10 m²/gm) $\gamma$-$Al_2O_3$ gel in pure titanium tetraisopropylate. The product was withdrawn from the liquid titanium compound and allowed to dry in moist air. The following reaction occurs:

$$Ti(OC_3H_7)_4 + 2H_2O \rightarrow TiO_2 + 4\ iso\text{-}C_3H_7OH$$

Thus, the $\gamma$-$Al_2O_3$ was treated with $TiO_2$. After exposure to moist air, the preparation was calcined in air at 540° C. for a period of 16 hours. Aqueous chloroplatinic acid was diluted to the desired strength and the catalyst impregnated by the method of incipient wetness with the platinum bearing solution. After drying the catalyst, the catalyst was again calcined in air at 540° C. for a period of 16 hours. The catalyst was analyzed as to composition and the following data were obtained:

| % Pt | 0.411 wt. % by wet techniques |
|---|---|
|  | 0.397 wt. % by X-ray techniques |
| % $TiO_2$ | 19.18 wt. %, or as |
| % Ti | 11.50 wt. % |
| Ratio Pt:Ti | 1:117 atoms |

The catalyst was also subjected to CO chemisorption, assuming 0.4 wt. (vide supra) % Pt on the catalyst, and the following data were obtained:

Chemisorption by the metal, cc/g: 0.52
Surface area, m²/g of metal: 264.75
Metal crystallite size, Å: 10.5

Both a standard Pt catalyst (Tables I and II) and Catalyst A, exemplary of this invention (Tables III and IV), were subjected to the tests outlined and previously explained. In the cyclohexane test, the test was conducted for a two day period, the catalysts being kept under flowing hydrogen between the tests. The following comparisons demonstrate that Catalyst A has activity and selectivity maintenance superior to the standard platinum catalyst in the dehydrogenation of cyclohexane to produce benzene at high temperatures, and the hydrogenation of benzene to produce cyclohexane at low temperatures.

TABLE I

CYCLOHEXANE DEHYDROGENATION TO BENZENE (First Day)
Standard Pt Catalyst: 0.3% Pt, 0.6% Cl on $\gamma$-$Al_2O_3$

| Wt. % Product | Time (Min) | | | | |
|---|---|---|---|---|---|
|  | 5.27 | 104.60 | 153.37 | 195.22 | 286.94 |
| $CH_4$ | 1.097 | 0.299 | 0.292 | 0.270 | 0.289 |
| $C_2$'s | 0.549 | 0.146 | 0.136 | 0.134 | 0.119 |
| $C_3$'s | 0.297 | 0.009 | 0.014 | 0 | 0 |
| $C_4$'s | 0.443 | 0.122 | 0.108 | 0.095 | 0.090 |
| i-$C_5$ | 0.267 | 0 | 0 | 0 | 0 |
| n-$C_5$ | 0.659 | 0.273 | 0.237 | 0.237 | 0.408 |
| 2,2-DMB | 0.112 | 0.055 | 0.007 | 0 | 0 |
| 2,3-DMB + 2-MP | 0.072 | 0.507 | 0.456 | 0.481 | 0.377 |
| 3-MP | 0 | 0 | 0 | 0 | 0 |
| n-$C_6$ | 0.417 | 0.316 | 0.228 | 0.276 | 0.299 |
| MCP | 0.130 | 4.504 | 4.843 | 4.839 | 4.789 |
| Cyc-$C_6$ | 0.445 | 55.971 | 62.762 | 67.506 | 70.482 |
| $\phi$H | 95.210 | 37.261 | 30.808 | 25.870 | 23.030 |

TABLE I-continued

CYCLOHEXANE DEHYDROGENATION TO BENZENE (First Day)
Standard Pt Catalyst: 0.3% Pt, 0.6% Cl on $\gamma$-$Al_2O_3$

| Wt. % Product | Time (Min) | | | | |
|---|---|---|---|---|---|
|  | 5.27 | 104.60 | 153.37 | 195.22 | 286.94 |
| n-$C_7$ | 0 | 0 | 0 | 0 | 0 |
| MCH | 0 | 0 | 0 | 0 | 0 |
| $\phi CH_3$ | 0.263 | 0.122 | 0.038 | 0.077 | 0 |
| Cumene | 0 | 0.040 | 0 | 0 | 0 |

TABLE II

CYCLOHEXANE DEHYDROGENATION TO BENZENE (Second Day)
Standard Pt Catalyst: 0.3% Pt, 0.6% Cl on $\gamma$-$Al_2O_3$

| Wt. % Product | Time (Min) | | | |
|---|---|---|---|---|
|  | 5.30 | 175.81 | 228.29 | 267.88 |
| $CH_4$ | 0.365 | 0.187 | 0.181 | 0.153 |
| $C_2$'s | 0.457 | 0.092 | 0.077 | 0.061 |
| $C_3$'s | 0 | 0 | 0 | 0 |
| $C_4$'s | 0.100 | 0.054 | 0.047 | 0.039 |
| i-$C_5$ | 0 | 0 | 0 | 0 |
| n-$C_5$ | 0.155 | 0.164 | 0.140 | 0.149 |
| 2,2-DMB | 0 | 0 | 0 | 0 |
| 2,3-DMB + 2-MP | 0.447 | 0.265 | 0.286 | 0.241 |
| 3-MP | 0 | 0 | 0 | 0 |
| n-$C_6$ | 0 | 0 | 0 | 0 |
| MCP | 0.536 | 2.017 | 3.354 | 3.275 |
| Cyc-$C_6$ | 72.301 | 77.959 | 81.398 | 82.722 |
| $\phi$H | 23.373 | 17.528 | 13.593 | 13.048 |
| n-$C_7$ | 0 | 0 | 0 | 0 |
| MCH | 0 | 0 | 0 | 0 |
| $\phi CH_3$ | 0 | 0 | 0 | 0.126 |
| Cumene | 0.046 | 0.039 | 0 | 0 |

TABLE III

CYCLOHEXANE DEHYDROGENATION TO BENZENE (First Day)
Catalyst A: 0.4% Pt, on 19% $TiO_2$ coated $\gamma$-$Al_2O_3$

| Time (Min) | 5.19 | 47.18 | 186.47 | 239.40 |
|---|---|---|---|---|
| Wt. % Product |  |  |  |  |
| $CH_4$ | 0.613 | 0.197 | 0.175 | 0.188 |
| $C_2$'s | 0.180 | 0.083 | 0.066 | 0.080 |
| $C_3$'s | 0.031 | 0.021 | 0.016 | 0.019 |
| $C_4$'s | 0.072 | 0.051 | 0.041 | 0.043 |
| i-$C_5$ | 0 | 0.020 | 0.049 | 0.056 |
| n-$C_5$ | 0 | 0.032 | 0.103 | 0.137 |
| 2,2-DMB | 0 | 0 | 0 | 0 |
| 2,3-DMB + 2-MP | 0 | 71.204 | 18.966 | 0.105 |
| 3-MP | 0 | 0 | 0 | 0.016 |
| n-$C_6$ | 0.047 | 0 | 0 | 0.216 |
| MCP | 0 | 0 | 0 | 1.318 |
| Cyc-$C_6$ | 9.643 | 4.132 | 2.819 | 2.559 |
| $\phi$H | 89.362 | 24.248 | 77.337 | 95.028 |
| n-$C_7$ | 0 | 0 | 0 | 0 |
| MCH | 0 | 0 | 0 | 0 |
| $\phi CH_3$ | 0 | 0 | 0.120 | 0 |
| Cumene | 0 | 0 | 0 | 0 |

TABLE IV

CYCLOHEXANE DEHYDROGENATION TO BENZENE (Second Day)
Catalyst A

| Wt. % Product | Time (Min) | | | | |
|---|---|---|---|---|---|
|  | 5.32 | 95.51 | 138.23 | 180.47 | 258.65 |
| $CH_4$ | 0.579 | 0.217 | 0.201 | 0.174 | 0.181 |
| $C_2$'s | 0.250 | 0.065 | 0.064 | 0.047 | 0.045 |
| $C_3$'s | 0.097 | 0.021 | 0.021 | 0.011 | 0.015 |
| $C_4$'s | 0.169 | 0.042 | 0.037 | 0.023 | 0.032 |
| i-$C_5$ | 0.147 | 0.040 | 0.036 | 0.021 | 0.025 |
| n-$C_5$ | 0.194 | 0.163 | 0.140 | 0.127 | 0.100 |
| 2,2-DMB | 0 | 0 | 0 | 0 | 0 |

TABLE IV-continued

CYCLOHEXANE DEHYDROGENATION TO BENZENE
(Second Day)

Catalyst A

| Wt. % Product | Time (Min) | | | | |
|---|---|---|---|---|---|
| | 5.32 | 95.51 | 138.23 | 180.47 | 258.65 |
| 2,3-DMB + 2-MP | 0.120 | 0.305 | 0.332 | 0.353 | 0.364 |
| 3-MP | 0.036 | 0.098 | 0.109 | 0.111 | 0.104 |
| n-$C_6$ | 0.192 | 0.313 | 0.303 | 0.250 | 0.277 |
| MCP | 0.073 | 0.243 | 0.293 | 0.344 | 0.382 |
| Cyc-$C_6$ | 0.469 | 0.765 | 0.751 | 0.876 | 1.107 |
| φH | 97.560 | 97.515 | 97.312 | 97.465 | 96.802 |
| n-$C_7$ | 0 | 0 | 0 | 0 | 0 |
| MCH | 0 | 0 | 0 | 0 | 0 |
| φ$CH_3$ | 0.106 | 0.206 | 0.110 | 0.126 | 0.133 |
| Cumene | 0 | 0 | 0 | 0 | 0.133 |

The data clearly show that the catalyst of this invention is superior for the noble metal type catalyzed dehydrogenation reaction.

Ultra stable clusters are formed by reaction between Group IVb, Vb, lanthanides, and actinades and Group VIII transition metals. The following example shows by varying the level of Pt and Ti that the formation of the cluster can accelerated or hindered depending on the level of the two constituents. It is therefore a phenomenological and inferential proof of the formation of the desired Pt-$TiO_2$ cluster. Since the Pt-$TiO_2$ displays enhanced noble metal activity and selectivity relative to Pt alone as a catalyst, the data presented by this example is for the cyclohexane reaction.

EXAMPLE 2

Catalyst B, employed in this example was prepared as follows: 0.69 g. titanium tetraisopropylate was weighed out and diluted to 80 cc with methylcyclopentane solvent. This solution was added to 100 g. of γ-$Al_2O_3$ (20–35 mesh) by incipient wetness and allowed to dry in moist air. The preparation was calcined at 540° C. for 16 hours. To 94.62 g. of this preparation 80 cc of a solution containing 287.5 mg Pt as hexachloroplatinic acid was added by incipient wetness. After drying the catalyst was calcined at 540° C. for 16 hrs. in air. Based on the amounts of reagents used the catalyst so prepared had a composition of 0.3 wt. % Pt and 0.1 wt. % Ti (ratio Pt:Ti is 10:13 atoms).

Catalyst C was prepared in similar manner to Catalyst B except that the quantities of titanium and platinum bearing compounds in the solutions were varied as follows: 3.0 g. of titanium tetraisopropylate, and 287.5 mg of Pt as hexachloroplatinic acid. The composition of the finished catalyst was 0.3 wt. % Pt and 1.0 wt. % Ti (ratio Pt:Ti is 1:14 atoms).

Catalyst D was prepared by the same procedure as Catalyst C, except that the quantities of titanium and platinum bearing compounds were again varied as follows: 6.0 g. of titanium tetraisoproylate, and 950 mg of Pt as hexachloroplatinic acid. The composition of the finished catalyst is 1.0 wt. % Pt and 0.5 wt. % Ti (ratio Pt:Ti is 1:2 atoms).

The performance data for conversion of cyclohexane to benzene for Catalysts B, C and D are presented in Tables V, VI and VII; these data clearly showing the effective level of metals which accelerate or decelerate the formation of the alloy of interest.

TABLE V

CYCLOHEXANE DEHYDROGENATION TO BENZENE
Catalyst B: 0.3% Pt, 0.1% Ti on γ-$Al_2O_3$

| Wt. % Product | Time (Min) | | | |
|---|---|---|---|---|
| | 4.94 | 69.78 | 114.83 | 157.56 |
| $CH_4$ | 0.579 | 0.273 | 0.277 | 0.278 |
| $C_2$'s | 0.509 | 0.162 | 0.158 | 0.142 |
| $C_3$'s | 0 | 0 | 0 | 0 |
| $C_4$'s | 0.188 | 0.220 | 0.121 | 0.114 |
| i-$C_5$ | 0 | 0 | 0.013 | 0.023 |
| n-$C_5$ | 0 | 0.061 | 0.028 | 0.013 |
| 2,2-DMB | 0.051 | 0.033 | 0.055 | 0.022 |
| 2,3-DMB + 2-MP | 0.326 | 0.275 | 0.237 | 0.237 |
| 3-MP | 0.014 | 0 | 0 | 0 |
| n-$C_6$ | 0 | 0 | 0 | 0 |
| MCP | 0.161 | 0.609 | 0.578 | 0.556 |
| Cyc-$C_6$ | 69.647 | 82.882 | 86.312 | 87.084 |
| φH | 24.574 | 12.217 | 9.757 | 8.985 |
| n-$C_7$ | 2.789 | 1.872 | 1.118 | 1.190 |
| MCH | 0 | 0 | 0 | 0 |
| Toluene | 0.330 | 0.302 | 0.148 | 0.136 |
| Cumene | 0 | 0 | 0 | 0 |

TABLE VI

CYCLOHEXANE DEHYDROGENATION TO BENZENE
Catalyst C: 0.3% Pt, 1.0% Ti on γ-$Al_2O_3$

| Wt. % Product | Time (Min) | | | | | |
|---|---|---|---|---|---|---|
| | 5.01 | 71.96 | 114.80 | 156.85 | 206.73 | 249.79 |
| $CH_4$ | 0.153 | 0.457 | 0.584 | 0.905 | 0.615 | 0.755 |
| $C_2$'s | 0.174 | 0.113 | 0.152 | 0.270 | 0.147 | 0.142 |
| $C_3$'s | 0.143 | 0.088 | 0.117 | 0.260 | 0.118 | 0.052 |
| $C_4$'s | 0.115 | 0.065 | 0.089 | 0.212 | 0.146 | 0.128 |
| i-$C_5$ | 0.063 | 0.059 | 0.112 | 0.169 | 0.048 | 0.019 |
| n-$C_5$ | 0.047 | 0.055 | 0.105 | 0.202 | 0.069 | 0.069 |
| 2,2-DMB | 0 | 0.028 | 0.053 | 0.072 | 0.036 | 0.058 |
| 2,3-DMB + 2-MP | 0.092 | 0.066 | 0.073 | 0.311 | 0.649 | 0.620 |
| 3-MP | 0.032 | 0.018 | 0.020 | 0.140 | 0.310 | 0.191 |
| n-$C_6$ | 0.034 | 0.031 | 0.025 | 0.124 | 0.433 | 0.350 |
| MCP | 0.140 | 0.047 | 0.043 | 0.227 | 1.872 | 3.207 |
| Cyc-$C_6$ | 0.166 | 0.115 | 0.088 | 0.150 | 4.849 | 23.630 |
| φH | 98.486 | 98.477 | 98.076 | 96.548 | 89.958 | 69.782 |
| n-$C_7$ | 0 | 0 | 0 | 0 | 0 | 0 |
| MCH | 0 | 0 | 0 | 0 | 0 | 0 |
| Toulene | 0.090 | 0.351 | 0.432 | 0.330 | 0.413 | 0.213 |
| Cumene | 0 | 0 | 0 | 0 | 0 | 0 |

TABLE VII

CYCLOHEXANE DEHYDROGENATION TO BENZENE
Catalyst D: 1.0% Pt, 0.5% Ti on γ-$Al_2O_3$ (13246-134-3)

| Wt. % Product | Time (Min) | | | | |
|---|---|---|---|---|---|
| | 5.06 | 48.84 | 187.01 | 228.82 | 270.90 |
| $CH_4$ | 2.611 | 0.537 | 0.442 | 0.449 | 0.433 |
| $C_2$'s | 0.399 | 0.157 | 0.184 | 0.199 | 0.198 |
| $C_3$'s | 0.067 | 0.055 | 0.070 | 0.106 | 0.103 |
| $C_4$'s | 0.119 | 0.107 | 0.112 | 0.147 | 0.156 |
| i-$C_5$ | 0.022 | 0.032 | 0.077 | 0.127 | 0.137 |
| n-$C_5$ | 0 | 0.019 | 0.034 | 0.094 | 0.087 |
| 2,2-DMB | 0.002 | 0 | 0.003 | 0.076 | 0.011 |
| 2,3-DMB + 2-MP | 0.003 | 0.003 | 0.007 | 0.030 | 0.029 |
| 3-MP | 0 | 0.003 | 0.002 | 0.005 | 0.009 |
| n-$C_6$ | 0.033 | 0 | 0.003 | 0.004 | 0 |
| MCP | 0.020 | 0.016 | 0.022 | 0.027 | 0.007 |
| Cyc-$C_6$ | 0.117 | 0.063 | 0.095 | 0.052 | 0.039 |
| φH | 95.375 | 98.524 | 98.481 | 98.261 | 98.325 |
| n-$C_7$ | 0 | 0 | 0 | 0 | 0 |
| MCH | 0.836 | 0 | 0 | 0 | 0 |
| Toluene | 0.341 | 0.392 | 0.437 | 0.379 | 0.448 |
| Cumene | 0 | 0.007 | 0.001 | 0 | 0 |

Comparisons of these results with the standard Pt catalyst of Example 1 show that even small amounts of Ti result in cluster formation (Table XIII), which gives an advantage in selectivity and activity maintenance. As the levels of Pt and/or Ti are raised, cluster formation becomes progressively easier, and activity and selectivity maintenance become progressively better. Comparisons of these data are presented, and summarized in Table VIII.

TABLE VIII

Activity and Selectivity Maintenance at End of Run for Cyclohexane Dehydrogenation

| Catalyst | Wt. % Pt | Wt. % Ti | Activity (% Conv.) | Selectivity ($\frac{Wt. \% \text{ Benzene}}{Wt. \% \text{ Conv.}} \times 100$) |
|---|---|---|---|---|
| Standard Pt Catalyst (Tables I and II) | 0.3 | — | 29.518 | 78.02 |
| Catalyst A (Tables III and IV) | 0.4 | 11.5 | 97.441 | 97.52 |
| Catalyst B (Table V) | 0.3 | 0.1 | 12.916 | 69.56 |
| Catalyst C (Table VI) | 0.3 | 1.0 | 76.370 | 91.37 |
| Catalyst D (Table VII) | 1.0 | 0.5 | 99.961 | 98.36 |

The data also indicate a threshhold below which the addition of Ti may have pejorative effects (Table V). But, above this level it is clear that either the Pt or Ti level may be varied either singly or simultaneously to enhance formation of the cluster and thus the performance properties of the catalyst.

Other Group IVB metals may also be used, as demonstrated by the following example.

EXAMPLE 3

In the preparation of this catalyst, herein after identified as Catalyst E, 255.73 g. of titanium tetraisopropylate and 47.17 g. of zirconium tetraisopropylate di-isopropanolate were first weighed out and mixed together (both are liquids at room temperature). The atom ratio between Ti and Zr in this mixture is 9:1.

To 200 g. of $\gamma$-Al$_2$O$_3$, 170 g. of the solution containing Ti and Zr was added by the method of incipient wetness. Based on the quantities of reagents, the finished support after drying in moist air and calcining for 16 hrs. in air at 540° C., has a composition of
 16.3 wt. % TiO$_2$
 2.9 wt. % ZrO$_2$
 80.8 wt. % Al$_2$O$_3$
To 100 g. of the suport, 67 cc of aqueous solution of hexachloroplatinic acid containing 300 mg of Pt was added by incipient wetness. After drying, the catalyst was calcined for six hours at 540° C.

Data are presented in Table IX for the dehydrogenation of cyclohexane to benzene over Catalyst E. Comparison of this data with the data in Table I (the standard Pt catalyst) show that Zr can be effectively substituted for Ti.

TABLE IX

CYCLOHEXANE DEHYDROGENATION TO BENZENE
Catalyst E: 0.3% Pt, 16.3% TiO$_2$, 2.9% ZrO$_2$
on $\gamma$-Al$_2$O$_3$ (13246-144-1)

| Wt. % Product | Time (Min) | | | |
|---|---|---|---|---|
| | 4.89 | 71.67 | 119.75 | 213.83 |
| CH$_4$ | 0.957 | 0.314 | 0.238 | 0.218 | 0.215 |
| C$_2$'s | 0.363 | 0.118 | 0.073 | 0.069 | 0.047 |
| C$_3$'s | 0.130 | 0.057 | 0.026 | 0.014 | 0 |
| C$_4$'s | 0.468 | 0.123 | 0.069 | 0.047 | 0.046 |
| i-C$_5$ | 0.147 | 0.054 | 0.036 | 0.031 | 0.035 |

TABLE IX-continued

CYCLOHEXANE DEHYDROGENATION TO BENZENE
Catalyst E: 0.3% Pt, 16.3% TiO$_2$, 2.9% ZrO$_2$
on $\gamma$-Al$_2$O$_3$ (13246-144-1)

| Wt. % Product | Time (Min) | | | |
|---|---|---|---|---|
| | 4.89 | 71.67 | 119.75 | 213.83 |
| n-C$_5$ | 0.315 | 0.109 | 0.081 | 0.063 | 0.062 |
| 2,2-DMB | 0.164 | 0.067 | 0.057 | 0 | 0.085 |
| 2,3-DMB + 2-MP | 0.114 | 0.209 | 0.112 | 0.138 | 0.121 |
| 3-MP | 0.154 | 0.278 | 0.195 | 0.205 | 0.213 |
| n-C$_6$ | 0 | 0.274 | 0.359 | 0.455 | 0.731 |
| MCP | 0 | 0 | 0 | 0 | 0 |
| Cyc-C$_6$ | 9.752 | 10.369 | 15.745 | 20.961 | 29.577 |
| $\phi$H | 91.583 | 84.123 | 79.444 | 73.630 | 64.619 |
| n-C$_7$ | 2.603 | 0 | 0 | 0 | 0 |
| MCH | 0 | 0 | 0 | 0 | 0 |
| $\phi$CH$_3$ | 1.029 | 0.616 | 0.350 | 0.453 | 0.310 |
| Cumene | 0 | 0 | 0 | 0.011 | 0 |

Other Group VIII metals may be used either with or in place of Pt. The following catalyst preparations and conversion data are exemplary.

EXAMPLE 4

A $\gamma$-Al$_2$O$_3$ support was prepared as in Example 1. Then 22.5 g. of titanium tetraisopropylate was added by the method of incipient wetness to 250 g. of $\gamma$-Al$_2$O$_3$ support. After allowing the preparation to dry in moist air it was calcined at 540° C. for 16 hrs., in air. Based on the quantity of reagents the support is 20.0 wt.% TiO$_2$.

Catalyst F was then prepared from 100 g. of the support by impregnation thereof with 80 cc of an aqueous solution containing 300 mg Pt from hexachloroplatinic acid and 300 mg Pd from tetrachloropalladic acid, by incipient wetness. After air drying, the catalyst was calcined at 540° C. for 16 hrs. in air. Based on the quantity of reagents used the catalyst was of composition having 0.3% Pt, 0.3% Pd, and 20.0% TiO$_2$ by wt.

Catalyst G was prepared in an analogous fashion to Catalyst F. To 50 g. of support as prepared in Example 1 was added 150 mg of Ir as chloroiridic acid, and 150 mg of Pt as hexachloroplatinic acid, the volume of the aqueous impregnating solution being 35 cc. Based on the quantity of reagents used, the catalyst has a composition of 0.3% Pt, 0.3% Ir, 20.0% TiO$_2$ by wt.

Data obtained by the dehydrogenation of cyclohexane with Catalysts F and G to produce benzene, given in Tables X and XI indicate the same phenomenon is occurring in the use of these catalysts as for Catalysts A–E.

TABLE X

CYCLOHEXANE DEHYDROGENATION TO BENZENE
Catalyst F: 0.3% Pt, 0.3% Pd, 20.0% TiO$_2$ on γ-Al$_2$O$_3$

| Wt. % Product | Time (Min) | | |
|---|---|---|---|
| | 179.21 | 224.10 | 267.06 |
| CH$_4$ | 0.239 | 0.244 | 0.185 |
| C$_2$'s | 0.036 | 0.033 | 0.028 |
| C$_3$'s | 0.029 | 0.011 | 0.006 |
| C$_4$'s | 0.091 | 0.048 | 0.035 |
| i-C$_5$ | 0.086 | 0.063 | 0.041 |
| n-C$_5$ | 0.188 | 0.234 | 0.146 |
| 2,2-DMB | 0.002 | 0 | 0 |
| 2,3-DMB + 2-MP | 0.368 | 0.383 | 0.345 |
| 3-MP | 0.085 | 0.084 | 0.090 |
| n-C$_6$ | 0.133 | 0.125 | 0.145 |
| MCP | 1.030 | 0.951 | 1.060 |
| Cyc-C$_6$ | 3.517 | 4.090 | 4.641 |
| φH | 93.999 | 93.524 | 92.989 |
| n-C$_7$ | 0 | 0 | 0 |
| MCH | 0 | 0 | 0 |
| Toluene | 0.153 | 0.080 | 0.160 |
| Cumene | 0 | 0 | 0 |

TABLE XI

CYCLOHEXANE DEHYDROGENATION TO BENZENE
Catalyst G: 0.3% Pt, 0.3% Ir, 20.0% TiO$_2$ on γ-Al$_2$O$_3$

| Wt. % Product | Time (Min) | | | |
|---|---|---|---|---|
| | 5.62 | 113.61 | 214.35 | 262.85 |
| CH$_4$ | 0.603 | 0.415 | 0.320 | 0.322 |
| C$_2$'s | 0.268 | 0.036 | 0.026 | 0 |
| C$_3$'s | 0.061 | 0 | 0 | 0 |
| C$_4$'s | 0.232 | 0.021 | 0.009 | 0 |
| i-C$_5$ | 0.028 | 0.003 | 0 | 0.028 |
| n-C$_5$ | 0.160 | 0.052 | 0.038 | 0 |
| 2,2-DMB | 0 | 0 | 0 | 0 |
| 2,3-DMB + 2-MP | 0 | 0.360 | 0.337 | 0.276 |
| 3-MP | 0 | 0.108 | 0.097 | 0.057 |
| n-C$_6$ | 17.854 | 3.925 | 3.355 | 2.607 |
| MCP | 4.588 | 2.876 | 1.528 | 1.542 |
| Cyc-C$_6$ | 8.495 | 10.945 | 13.494 | 16.451 |
| φH | 23.264 | 80.241 | 80.204 | 78.437 |
| n-C$_7$ | 0 | 0 | 0 | 0 |
| MCH | 0 | 0 | 0 | 0 |
| Toluene | 0 | 0.119 | 0.216 | 0.241 |
| Cumene | 0 | 0 | 0 | 0 |

Other promoters may be used in conjunction with the Pt-TiO$_2$ cluster catalyst previously described.

EXAMPLE 5

Catalyst H was prepared in the following manner: To 50 g. of a support similar to that described in Example 4 was added by incipient wetness technique 35 cc of an aqueous solution containing 150 mg Pt from hexachloroplatinic acid and 156 mg Re from perrhenic acid. Crushed dry ice was added to the preparation, and the preparation was then dried at 74° C. for 16 hrs. The catalyst was calcined at 540° C. for 16 hrs. in air. Based on the quantity of reagents used the catalyst has a composition of 0.3% Pt, 0.3% Re, 20.0% TiO$_2$ by wt. Data on the use of this catalyst to dehydrogenate cyclohexane taken on the record day of operation are presented in Table XII.

TABLE XII

Cyclohexane Dehydrogenation to Benzene
(Second Day)

| Wt. % Product | Time (Min) | | | |
|---|---|---|---|---|
| | 5.27 | 108.06 | 163.86 | 290.04 |
| Cyc-C$_6$ | 18.416 | 42.902 | 52.442 | 55.844 |
| Benzene | 68.605 | 52.979 | 43.474 | 40.308 |

TABLE XII-continued

Cyclohexane Dehydrogenation to Benzene
(Second Day)

| Wt. % Product | Time (Min) | | | |
|---|---|---|---|---|
| | 5.27 | 108.06 | 163.86 | 290.04 |
| Other | 12.979 | 4.119 | 4.084 | 3.848 |

These data clearly demonstrate that the cluster formation is present and that catalyst performance is superior to the standard Pt reference catalyst.

In Example 1, the superior activity and selectivity maintenance of the Pt-Ti alloy catalyst was demonstrated for noble metal type reactions. However, the catalyst was less effective for those reactions which in addition to the noble metal activity component also required an additional component, or components to affect the desired conversion at high levels of activity and selectivity maintenance, e.g., reactions involving the conversion of methylcyclopentane and normal heptane.

When the catalyst is so constituted that the Group IV-B or V-B metal oxide does not cover the surface of the support, additional promoters may be used to incorporate additional functionality. For example in the case of an alumina gel, halide may be added to increase the isomerization and cyclization functionality of the catalyst.

The following data are thus presented to show that other components can be incorporated into the catalysts to provide additional functions, without adverse effect on the functions produced by the added metal components.

EXAMPLE 6

To affect the desired comparisons the following catalysts were prepared:

Catalyst I was prepared as follows: A solution of hexachloroplatinic acid containing 1000 mg of Pt was diluted to 83 cc with water and added to 100 g of γ-Al$_2$O$_3$, by the method of incipient wetness. The preparation was allowed to dry and calcined for 16 hrs. at 540° C. in air. Based on the composition of the reagents the catalyst is 1.0 wt. % Pt and 1.1 wt. % Cl.

Catalyst J was prepared as follows: A solution was made up which contained 1.2 cc of concentration aqueous hydrochloric acid in a 38 cc volume. This solution was added to 50 g. of a catalyst similar to Catalyst D of Example 2, which was already impregnated with Pt in a concentration of 1.0 wt. %, and Ti in concentration of 0.5 wt. %. The chloride level of the impregnating solution was chosen to bring the additional quantity of halide to 0.5 g. for the entire preparation, impregnation being by incipient wetness. After drying the catalyst was calcined at 540° C. in air for eight hours. Data for both Catalysts I and J are presented in Tables XIII, XIV, XV, XVI, XVII, and XVIII with cyclohexane, methylcyclopentane and n-heptane feeds.

TABLE XIII

CYCLOHEXANE DEHYDROGENATION TO BENZENE
Catalyst I: 1.0% Pt on γ-Al$_2$O$_3$

| Wt. % Product | Time (Min) | | | | |
|---|---|---|---|---|---|
| | 4.56 | 71.57 | 122.51 | 165.59 | 214.63 |
| CH$_4$ | 6.913 | 2.395 | 2.009 | 1.897 | 1.869 |
| C$_2$'s | 0 | 0.449 | 0.346 | 0.338 | 0.407 |
| C$_3$'s | 0 | 0 | 0.088 | 0.096 | 0.116 |
| C$_4$'s | 0.040 | 0.135 | 0.151 | 0.181 | 0.215 |

TABLE XIII-continued

CYCLOHEXANE DEHYDROGENATION TO BENZENE

Catalyst I: 1.0% Pt on γ-$Al_2O_3$

| Wt. % Product | Time (Min) | | | | |
|---|---|---|---|---|---|
| | 4.56 | 71.57 | 122.51 | 165.59 | 214.63 |
| i-$C_5$ | 0 | 0.003 | 0 | 0 | 0.092 |
| n-$C_5$ | 0.003 | 0.004 | 0 | 0 | 0 |
| 2,2-DMB | 0 | 0.003 | 0 | 0 | 0 |
| 2,3-DMB + 2-MP | 0 | 0.001 | 0.012 | 0 | 0 |
| 3-MP | 0 | 0 | 0 | 0 | 0 |
| n-$C_6$ | 0 | 0.001 | 0.012 | 0 | 0 |
| MCP | 0.030 | 0.027 | 0.037 | 0.020 | 0.015 |
| Cyc-$C_6$ | 0.029 | 0.013 | 0.024 | 0 | 0.009 |
| φH | 91.759 | 96.488 | 96.725 | 96.818 | 96.684 |
| n-$C_7$ | 0 | 0 | 0 | 0 | 0 |
| MCH | 0 | 0 | 0 | 0 | 0 |
| Toluene | 0.495 | 0.466 | 0.447 | 0.578 | 0.552 |
| Cumene | 0 | 0 | 0.126 | 0.025 | 0 |

TABLE XIV

METHYLCYCLOPENTANE CONVERSION TO BENZENE

Catalyst I: 1.0% Pt, on γ-$Al_2O_3$

| Wt. % Product | Time (Min) | | | | | |
|---|---|---|---|---|---|---|
| | 4.82 | 74.60 | 120.67 | 166.65 | 218.63 | 1.461 |
| $CH_4$ | 6.384 | 2.436 | 1.889 | 1.707 | 1.567 | 1.461 |
| $C_2$'s | 1.383 | 0.522 | 0.435 | 0.336 | 0.332 | 0.229 |
| $C_3$'s | 0 | 0.093 | 0 | 0 | 0 | 0 |
| $C_4$'s | 1.716 | 0.718 | 0.457 | 0.450 | 0.375 | 0.355 |
| i-$C_5$ | 0.171 | 0.095 | 0.119 | 0.056 | 0.026 | 0.017 |
| n-$C_5$ | 0.384 | 0.391 | 0.284 | 0.230 | 0.197 | 0.197 |
| 2,2-DMB | 0.640 | 0.290 | 0.173 | 0.204 | 0.168 | 0.127 |
| 2,3-DMB + 2-MP | 1.776 | 1.324 | 1.017 | 1.102 | 0.972 | 0.878 |
| 3-MP | 0 | 0.222 | 0.167 | 0 | 0 | 0 |
| n-$C_6$ | 0 | 0.653 | 0.552 | 0.554 | 0.497 | 0.466 |
| MCP | 67.535 | 66.512 | 68.961 | 69.764 | 70.476 | 72.046 |
| Cyc-$C_6$ | 8.266 | 12.299 | 14.167 | 14.125 | 13.860 | 13.888 |
| φH | 9.572 | 10.380 | 7.955 | 7.474 | 7.675 | 6.544 |
| n-$C_7$ | 0 | 0 | 0 | 0 | 0 | 0 |
| MCH | 0 | 0 | 0 | 0 | 0 | 0 |
| φ$CH_3$ | 0.419 | 0.479 | 0.362 | 0.328 | 0.238 | 0.251 |
| Cumene | 0 | 0 | 0.175 | 0.308 | 0.306 | 0.264 |

TABLE XV

NORMAL HEPTANE DEHYDROCYCLIZATION TO TOLUENE

Catalyst I: 1.0% Pt, on γ-$Al_2O_3$

| Wt. % Product | Time (Min) | | | | | |
|---|---|---|---|---|---|---|
| | 4.73 | 76.60 | 119.62 | 164.65 | 217.67 | 259.70 |
| $CH_4$ | 34.972 | 16.777 | 12.945 | 11.586 | 15.513 | 13.365 |
| $C_2$'s | 8.888 | 6.202 | 5.002 | 4.556 | 6.138 | 5.434 |
| $C_3$'s | 2.143 | 2.482 | 2.042 | 1.867 | 2.494 | 2.088 |
| $C_4$'s | 9.630 | 6.617 | 5.463 | 5.026 | 6.472 | 5.891 |
| i-$C_5$ | 2.853 | 4.674 | 4.122 | 3.684 | 4.486 | 4.024 |
| n-$C_5$ | 3.011 | 4.328 | 4.144 | 3.998 | 4.810 | 4.689 |
| 2,2-DMB | 1.636 | 1.465 | 1.596 | 1.398 | 1.784 | 1.705 |
| 2,3-DMB + 2-MP | 1.241 | 1.172 | 1.514 | 1.321 | 1.661 | 1.500 |
| 3-MP | 0 | 0.244 | 0.493 | 0.369 | 0.579 | 0.381 |
| n-$C_6$ | 0.220 | 0.256 | 0.591 | 0.631 | 0.833 | 0.745 |
| MCP | 2.439 | 1.591 | 1.916 | 1.977 | 2.461 | 2.227 |
| Cyc-$C_6$ | 0.370 | 1.054 | 1.922 | 2.739 | 3.271 | 3.872 |
| φH | 14.540 | 12.549 | 10.577 | 10.123 | 10.019 | 10.521 |
| n-$C_7$ | 6.434 | 3.969 | 4.614 | 6.564 | 7.161 | 9.539 |
| MCH | 0 | 0 | 0.149 | 0.227 | 0.854 | 1.105 |
| φ$CH_3$ | 10.462 | 35.620 | 41.075 | 41.797 | 29.636 | 30.903 |
| Cumene | 0 | 0 | 0.330 | 0.428 | 0.479 | 0.319 |

TABLE XVI

CYCLOHEXANE DEHYDROGENATION TO BENZENE

Catalyst J: 1.0% Pt, 0.5% Ti on γ-$Al_2O_3$, Chloride Enhanced

| Wt. % Product | Time (Min) | | | |
|---|---|---|---|---|
| | 4.60 | 70.55 | 112.73 | 157.65 |
| $CH_4$ | 4.594 | 2.012 | 1.591 | 1.782 |
| $C_2$'s | 0 | 0.430 | 0.380 | 0.431 |
| $C_3$'s | 0 | 0.115 | 0.102 | 0.126 |
| $C_4$'s | 0.031 | 0.172 | 0.166 | 0.245 |
| i-$C_5$ | 0.003 | 0.030 | 0.011 | 0.042 |
| n-$C_5$ | 0.048 | 0 | 0 | 0.020 |
| 2,2-DMB | 0.042 | 0 | 0.004 | 0 |
| 2,3-DMB + 2-MP | 0 | 0 | 0 | 0.003 |
| 3-MP | 0.006 | 0 | 0.004 | 0.001 |
| n-$C_6$ | 0.011 | 0 | 0.009 | 0.002 |
| MCP | 0.074 | 0.029 | 0.034 | 0.031 |
| Cyc-$C_6$ | 0 | 0.016 | 0.007 | 0.036 |
| φH | 94.398 | 96.573 | 97.127 | 96.683 |
| n-$C_7$ | 0 | 0 | 0 | 0 |
| MCH | 0 | 0 | 0 | 0 |
| φ$CH_3$ | 0.598 | 0.618 | 0.537 | 0.527 |
| Cumene | 0 | 0 | 0 | 0 |

TABLE XVII

METHYLCYCLOPENTANE CONVERSION TO BENZENE

Catalyst J: 1.0% Pt, 0.5% Ti on γ-$Al_2O_3$

| Wt. % Product | Time (Min) | | | | |
|---|---|---|---|---|---|
| | 4.66 | 79.67 | 129.55 | 171.69 | 226.73 |
| $CH_4$ | 3.530 | 1.576 | 1.369 | 1.276 | 1.420 |
| $C_2$'s | 0.991 | 0.422 | 0.394 | 0.306 | 0.304 |
| $C_3$'s | 0 | 0 | 0 | 0 | 0 |
| $C_4$'s | 1.091 | 0.605 | 0.473 | 0.425 | 0.456 |
| i-$C_5$ | 0.064 | 0.062 | 0.049 | 0.031 | 0.043 |
| n-$C_5$ | 0.239 | 0.219 | 0.0170 | 0.133 | 0.169 |
| 2,2-DMB | 0.398 | 0.206 | 0.165 | 0.148 | 0.164 |
| 2,3-DMB + 2-MP | 1.200 | 0.929 | 0.795 | 0.690 | 0.733 |
| 3-MP | 0 | 0.454 | 0.594 | 0.544 | 0.545 |
| n-$C_6$ | 1.190 | 2.572 | 2.670 | 2.599 | 2.680 |
| MCP | 77.368 | 74.145 | 74.468 | 75.177 | 75.433 |
| Cyc-$C_6$ | 6.793 | 10.383 | 10.915 | 11.098 | 11.014 |
| φH | 6.567 | 7.769 | 7.302 | 6.948 | 6.608 |
| n-$C_7$ | 0 | 0 | 0 | 0 | 0 |
| MCH | 0 | 0 | 0 | 0 | 0 |
| φ$CH_3$ | 0.358 | 0.328 | 0.346 | 0.322 | 0.246 |
| Cumene | 0 | 0.014 | 0.012 | 0.019 | 0 |

TABLE XVIII

NORMAL HEPTANE DEHYDROCYCLIZATION TO TOLUENE

Catalyst J: 1.0% Pt, 0.5% Ti on γ-$Al_2O_3$

| Wt. % Product | Time (Min) | | | | | |
|---|---|---|---|---|---|---|
| | 4.75 | 77.70 | 119.68 | 163.60 | 205.72 | 247.69 |
| $CH_4$ | 31.627 | 13.278 | 9.944 | 8.747 | 8.174 | 8.269 |
| $C_2$'s | 10.076 | 6.311 | 4.913 | 4.702 | 4.455 | 4.504 |
| $C_3$'s | 3.048 | 2.679 | 2.129 | 2.064 | 1.999 | 1.952 |
| $C_4$'s | 10.815 | 7.050 | 5.457 | 5.188 | 4.892 | 4.918 |
| i-$C_5$ | 3.906 | 5.459 | 4.281 | 3.990 | 3.604 | 3.561 |
| n-$C_5$ | 3.738 | 5.396 | 4.541 | 4.367 | 4.123 | 3.996 |
| 2,2-DMB | 1.817 | 1.839 | 1.719 | 1.725 | 1.827 | 1.738 |
| 2,3-DMB + 2-MP | 1.508 | 1.605 | 1.539 | 1.529 | 1.464 | 1.407 |
| 3-MP | 0 | 0.547 | 0.465 | 0.546 | 0.422 | 0.437 |
| n-$C_6$ | 0.286 | 0.761 | 0.712 | 0/797 | 0.683 | 0.702 |
| MCP | 2.270 | 2.219 | 2.118 | 2.162 | 2.305 | 2.240 |
| Cyc-$C_6$ | 0.362 | 2.236 | 2.942 | 3.845 | 4.213 | 4.684 |
| φH | 13.876 | 10.614 | 10.582 | 9.682 | 9.791 | 11.290 |
| n-$C_7$ | 3.469 | 4.952 | 5.943 | 8.693 | 10.177 | 10.766 |
| MCH | 0 | 0.533 | 1.029 | 1.204 | 1.078 | 1.158 |
| φ$CH_3$ | 12.422 | 32.672 | 39.062 | 37.884 | 36.980 | 35.175 |
| Cumene | 0.026 | 0.119 | 0.232 | 0.241 | 0.233 | 0.169 |

Comparisons of the performance of Catalysts I and J show that both catalysts have the same activity and selectivity maintenance for the reaction against cyclohexane (Tables XIII and XIV). Catalyst J is somewhat less effective for the reaction against methylcyclopentane (Tables XIV and XVI). However, a major advance has been accomplished in that the end-of-run performance is clearly superior when normal heptane is used as a feed (Tables XV and XVII).

Thus other functionalities can be incorporated in catalysts which contain the Pt-Ti or similar alloys or clusters as the active metal component without negatively affecting the performance of the metal component.

EXAMPLE 7

The purpose of this example is to demonstrate the surface heterogeneity of the catalysts of the present invention.

Before discussing the experimental results which lead to the above conclusion, a brief discussion of the experimental technique arriving at the data is offered, to wit:

Ion scattering spectrometry is a recent technique developed for examining the surfaces of materials. Briefly it consists of directing a stream of noble gas ions at the surface and examining the scattering pattern of the elastically scattered ions.

Calibration and analysis of the elastically scattered ions reveals characteristic scattering patterns for each different element on the surface. Thus analysis of the elastically scattered noble gas ions will give a gross indication of the surface composition.

Where such a measurement is preformed for a support containing 19 wt. % $TiO_2$ on $\gamma$-$Al_2O_3$ prepared by the method of this invention, the ion scattering spectrum shows a surface composition containing both Ti and Al in addition to O. If the $TiO_2$ were present as an epitaxial layer, and there is sufficient $TiO_2$ in the preparation tested in this example for it to exist as an epitaxial layer, then the ion scattered spectrum would show only Ti and O on the surface. Conversely if there were no $TiO_2$ present in the preparation the ion scattered spectrum would show only Al and O. Since Ti, Al, and O constitute the elements on the surface then the $TiO_2$ present can not be existing as an epitaxial layer because Al is at the surface. If, on the other hand, the $Al_2O_3$ was covered by an epitaxial layer of $TiO_2$ it would not be detected. Thus the surface is either heterogeneous being composed of clusters of $TiO_2$ on the $\gamma$-$Al_2O_3$, or is constituted of a mixed oxide containing Ti and Al.

X-ray powder diffraction studies show crystallographic lines characteristic of the anatase form of $TiO_2$ being present in this preparation. Since crystallites must be of 50 Angstrom units or greater in size to be detected by X-ray, at least some of the $TiO_2$ on the surface of $\gamma$-$Al_2O_3$ exists as clusters of $TiO_2$ in the anatase form.

EXAMPLE 8

This example shows that $TiO_2$ supported on $\gamma$-$Al_2O_3$ as characterized in Example 7 behaves differently from unsupported $TiO_2$ and therefore a novel state of matter exists on the surface of the preparation.

The preparations characterized in Table XIX (referred to as A, B, C, D and E) were examined by dynamic oxygen chemisorption techniques.

TABLE XIX

| | | |
|---|---|---|
| A. | $\gamma$-$Al_2O_3$ gel | (a gel well known to the art) |
| B. | $TiO_2$ gel | (as per U.S. Pat. No. 3,092,457) |
| C. | 19% $TiO_2$ on $\gamma$-$Al_2O_3$ | (a support prepared in accordance with the teachings of this invention) |
| D. | 0.4% Pt on 19% $TiO_2$ on $\gamma$-$Al_2O_3$ | (a catalyst prepared in accordance with the teachings of this invention) |
| E. | 0.3% Pt on $\gamma$-$Al_2O_3$ | (a conventional Pt on $\gamma$-$Al_2O_3$ catalyst known to the art) |

The $\gamma$-$Al_2O_3$ preparation designated A is common to all five preparations A–E. The temperature of the hydrogen reduction step prior to chemisorption with oxygen was varied. Chemisorption measurements were made at 25° C. The data presented in Table XX were obtained:

TABLE XX

Oxygen Chemisorption Data
$O_2$ Titers ($\mu$ Moles/gm)

| Sample | $H_2$ Reduction Temperature, °C. | |
|---|---|---|
| | 25 | 482 |
| $Al_2O_3$ (A) | 0.00 | 0.00 |
| Anatase $TiO_2$ Gel (B) | 0.00 | 26.55 |
| 19% $TiO_2$/$Al_2O_3$ (C) | 0.00 | 36.10 |
| 0.4% Pt/19% $TiO_2$/$Al_2O_3$ I (D) | 19.04 | 48.10 |
| 0.3% Pt/$Al_2O_3$ (E) | 11.32 | 11.65 |

Varying the temperature of hydrogen reduction, as noted, does not affect the oxygen chemisorption of the $\gamma$-$Al_2O_3$ used. Over the temperature range studied, the $\gamma$-$Al_2O_3$ is shown to be inactive for oxygen chemisorption.

In contrast, the $TiO_2$ gel and the supported $TiO_2$ on $\gamma$-$Al_2O_3$ can be made oxygen chemisorption active by reducing the support at progressively higher temperatures. As the temperature is increased during the hydrogen reduction, progressively more of the $TiO_2$ is reduced. The supported $TiO_2$ on $\gamma$-$Al_2O_3$ is thus rendered more active for the reoxidation which occurs during oxygen chemisorption. However, the supported form of $TiO_2$ is approximately seven times more active for oxygen chemisorption than the unsupported form of $TiO_2$. This comparison is based on the relative titers of $O_2$ chemisorbed after reduction at 482° C. with hydrogen making allowances for the fact that the $TiO_2$ gel is essentially 100% $TiO_2$ and the supported $TiO_2$ containing preparation contains only 19% $TiO_2$.

Allowing for concentration differences in the amount of Pt in the two Pt continuing samples and postulating somewhat different degrees of dispersion leads to the conclusion that the Pt is contributing a constant, reduction-temperature independent, amount of oxygen chemisorption activity.

EXAMPLE 9

Supports containing various amounts of $TiO_2$ (alternatively expressed as Ti) were prepared. Each of these supports were impregnated with $H_2PtCl_6$ by incipient wetness to give a final platinum level on the resulting catalyst of approximately 0.3% by weight. The preparations were dried in air at ambient conditions and calcined at 540° C. for 16 hours in air. Each of these preparations was reduced in flowing hydrogen and tested for cyclohexane dehydrogenation activity at 0 psig, 495° C., 1.3 W/Hr/W. Each catalyst had initially a very high selectivity and activity for the conversion of cyclohexane to benzene. After four hours this activity and selectivity declined to a level characteristic of the catalyst preparation. Referring to the enclosed figure, the gas chromatographic weight percent benzene in the product after four hours of feeding cyclohexane under standard conditions is plotted in the figure as a function of the weight percent of Ti in the catalyst since all other variables remain constant. With one exception (as appears represented by an erratic data point), the data demonstrate the initiation of a stabilizing interaction between Pt and some form of Ti which increases with increasing Ti content reaching 90% of the effect at Ti loadings as low as 1.5 wt. % Ti.

The data clearly demonstrates that the catalyst compositions of this invention possess an unusual stability against deactivation when used to conduct hydrogenation and dehydrogenation reactions. For example, in runs conducted at atmospheric pressure to form benzene by dehydrogenation of cyclohexane catalyst compositions comprised of Pt/TiO$_2$ clusters have been composed at similar operating conditions with catalysts otherwise similar except that they were constituted only of Pt, with the result that the initially high activity of Pt catalyst experienced an exponential decay after start-up, whereas the catalyst compositions containing the Pt/TiO$_2$ clusters maintained the initial high level of conversion throughout the runs. Whereas the reasons for this difference in the activity maintenance of the two different catalysts is not known, analysis of these catalysts via chemisorption techniques had led to the hypothesis of the existance of a defect or suboxide TiO$_{2-x}$ phase which varies in reducibility, but once reduced leads to the formation of localized clusters on the surface of the catalysts. Catalysts which contain these localized clusters unlike those which do not contain such clusters have demonstrated a dramatic increase in stability, demonstrating some type of interaction between the Pt and TiO$_2$, or between the Pt, TiO$_2$ and the support since the number of defects in a bulk TiO$_2$ gel are found to be increased when the TiO$_2$ gel is combined with a support, notably alumina. In any regard, it has been clearly demonstrated that the properties of Group VIII metals are significantly, beneficially modified by the inclusion of Group IV-B metals to form clusters of the Group VIII and Group IV-B metals.

Having described the invention, what is claimed is:

1. A catalyst useful for the conversion of a hydrocarbon feed by contact thereof at hydrocarbon conversion conditions which comprises a cluster of titanium metal oxide and a Group VIII noble metal deposited on the surface of an inorganic oxide support.

2. The composition of claim 1 wherein clusters of said titanium metal oxide and Group VIII noble metal are separated by areas of support surface which contain little, if any, of said titanium metal oxide, or clusters of said titanium metal oxide and Group VIII noble metal.

3. The composition of claim 2 wherein the support surface is alumina.

4. The composition of claim 1 wherein the support surface is alumina.

5. The composition of claim 1 wherein the Group IV-B metal oxide is titanium oxide.

6. The composition of claim 1 wherein the Group VIII metal is platinum.

7. The composition of claim 1 wherein the Group IV-B metal oxide is titanium oxide and the Group VIII metal is platinum.

8. A process for the preparation of novel catalyst compositions which comprises forming a nonaqueous solution of a compound, or compounds, of titanium metal, contacting an inorganic metal oxide support with said solution to impregnate said solution into said support, drying and calcining said support in a moist atmosphere to form and deposit titanium metal oxide onto said support surface, and contacting said impregnated support with a solution of a Group VIII noble metal compound to form clusters of said titanium metal oxide and Group VIII noble metal on the surface of said support, and thereafter, drying and calcining said support.

9. The process of claim 8 wherein the support surface is alumina.

10. The process of claim 8 wherein the titanium oxide is formed and deposited on an alumina suport.

11. The process of claim 8 wherein the Group VIII noble metal is platinum.

12. The process of claim 8 wherein the titanium oxide is formed and deposited on an alumina support, the Group VIII noble metal is added to the titanium oxide containing support and the Group VIII noble metal is platinum.

13. The process of claim 8 wherein the clusters are separated by areas of support surface which contain little, it any, of said titanium metal oxide, or clusters of said titanium metal oxide and Group VIII noble metal.

14. The process of claim 13 wherein the support surface is alumina.

* * * * *